United States Patent [19]

Huber et al.

[11] Patent Number: 4,990,443

[45] Date of Patent: Feb. 5, 1991

[54] HAPTEN-PROTEIN CONJUGATES AND METHODS OF USE IN IMMUNOASSAYS

[75] Inventors: Erasmus Huber, Garching; Christian Klein, Weilheim; Gunter Pappert, Tutzing; Klaus Hallermayer, Munich, all of Fed. Rep. of Germany

[73] Assignee: Boehringer Mannheim GmbH, Mannheim, Fed. Rep. of Germany

[21] Appl. No.: 301,582

[22] Filed: Jan. 24, 1989

[30] Foreign Application Priority Data

Jan. 25, 1988 [DE] Fed. Rep. of Germany ....... 3802060
Sep. 29, 1988 [DE] Fed. Rep. of Germany ....... 3833149

[51] Int. Cl.$^5$ .................... C12Q 1/54; G01N 33/535
[52] U.S. Cl. ........................................ 435/7.9; 435/14;
435/28; 435/7.92; 435/961; 436/543; 530/350;
530/402; 530/403; 530/405
[58] Field of Search .................... 260/397; 435/28, 7,
435/14; 436/543; 530/350, 402, 403, 405

[56] References Cited

FOREIGN PATENT DOCUMENTS 0114011 7/1984 European Pat. Off. .
2814776 10/1978 Fed. Rep. of Germany .

OTHER PUBLICATIONS

Janoski et al.—Steroids, vol. 23 (1974), pp. 49–59.
Megges et al.—Chem. Abst. vol. 109 (1988), p. 93436d, original article, May, 1987.
Saltykova et al.—Chem. Abst. vol. 92 (1980), p. 198642b.
Yamauchi et al.—Chem. Abst. vol. 100 (1984), p. 49722j.
Janoski et al.—Chem. Abst. vol. 81 (1974), p. 35229f.
Zorina et al.—Chem. Abst. vol. 93 (1980), p. 46970q.

Primary Examiner—Sam Rosen
Attorney, Agent, or Firm—Felfe & Lynch

[57] ABSTRACT

The present invention provides hapten derivatives of the general formula:

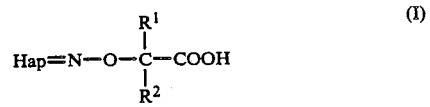

wherein Hap is a residue formed from a hapten carrying a keto or aldehyde group by splitting off an oxo group and $R^1$ and $R^2$, which can be the same or different, are alkyl radicals containing up to 7 carbon atoms and one of the symbols $R^1$ and $R^2$ can also represent a hydrogen atom.

The present invention also provides hapten-protein conjugates of the general formula:

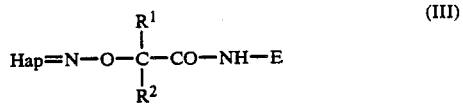

wherein Hap, $R^1$ and $R^2$ have the above-given meanings and E—NH is the residue of a protein bound via an $\epsilon$-amino group of a lysine residue.

9 Claims, 1 Drawing Sheet

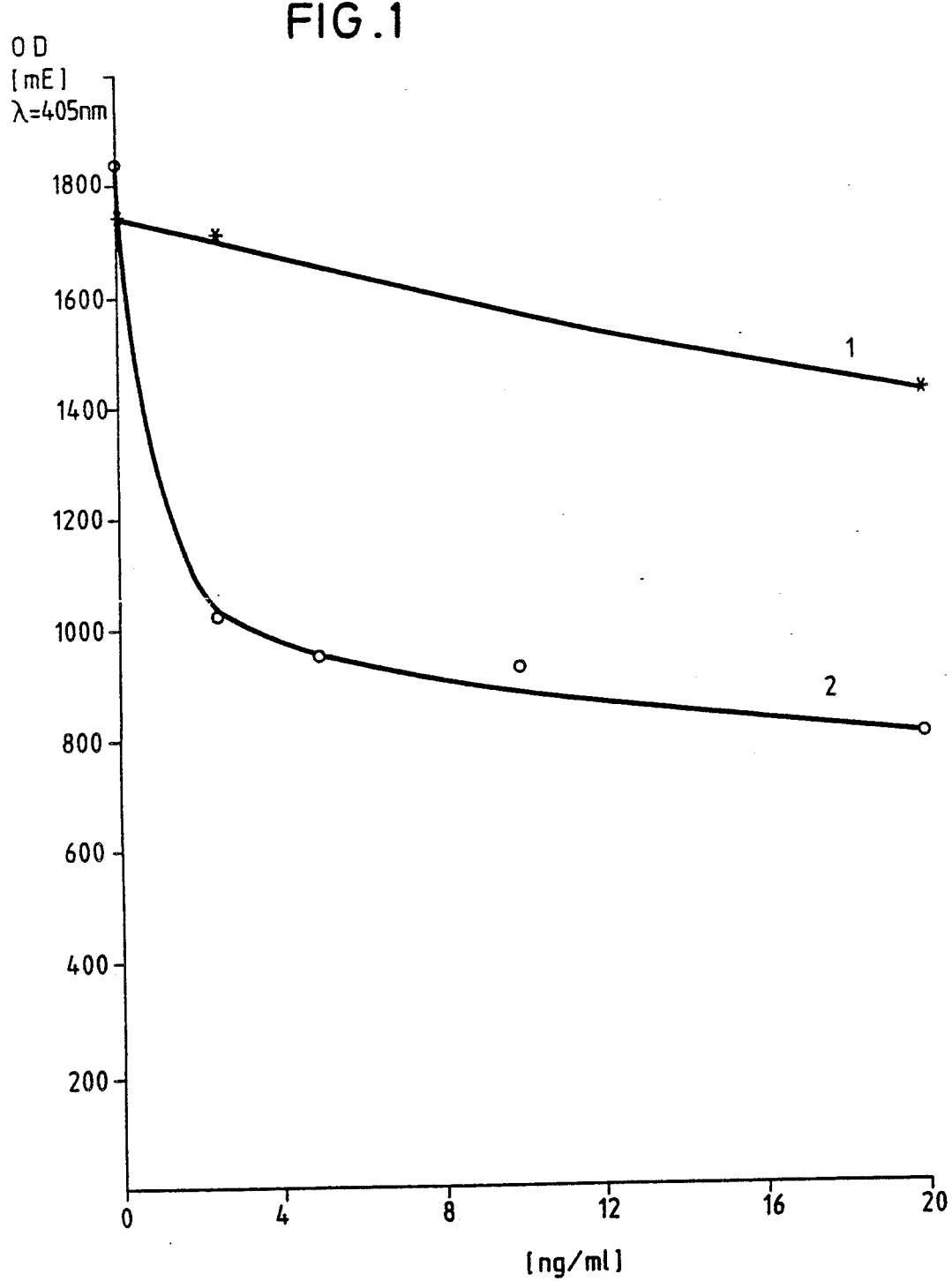

HAPTEN-PROTEIN CONJUGATES AND METHODS OF USE IN IMMUNOASSAYS

The present invention is concerned with new hapten derivatives and with hapten-protein conjugates derived therefrom.

In clinical diagnosis, determination processes following immunoassay principles are being carried out to an increasing extent, these processes being characterized by increased sensitivity. There are very many process variants of immunoassays which are available. For many purposes, competitive assays are carried out. In this case, the substance to be determined and a known amount of the substance to be determined, which is labelled with an enzyme and is added to the sample, compete for an antibody.

Therefore, there is a need for conjugates of a labelling system and of a compound specifically bindable with the substance to be determined or with an antibody, in which the conjugate may only react with the substance to be determined or with the antibody and does not display any cross-reactivities with other compounds present in the sample solution in order not to falsify the result. Since the specifically binding substance and the labelling enzyme are frequently not bound directly with one another but rather are coupled via a linking grouping (spacer), the affinity of the antibody to the spacer can give rise to problems.

Furthermore, there is a great need for specific antibodies. In general, antibodies are produced by injecting an immunogen, such as an antigen or hapten, in appropriate form several times into an organism capable of antibody formation. According to definition, haptens are molecules with a molecular weight of less than 1000 Dalton which alone are not immunogenically effective but become immunogenic by binding to a protein. For the immunization, the hapten is conjugated with an immunogenic molecule, for example a serum protein. When such a conjugate is injected, then, besides anti-protein antibodies, the organism also forms the desired anti-hapten antibodies, the antibodies formed then being obtained from the organism. In this way, polyclonal antibodies can be obtained.

Also for the production of monoclonal antibodies, there must first be carried out an immunization of appropriate organisms, as a rule mice. Due to the usual repeated injection of an antigen or hapten conjugate, a B cell is induced to synthesise antibodies against this antigen or hapten and to secrete them. By means of screening, a B cell which produces the desired antibodies is isolated from the spleen and immortalized by fusion with a myeloma cell. These cells then continuously produce the same monoclonal antibody.

For the binding of haptens which have keto or aldehyde functions to a protein, a conventional method is to react the carbonyl function with 0-(carboxymethyl)-hydroxylamine to give an oxime and to couple via the free carboxyl function to ε-amino groups of the high molecular weight carrier molecule (cf. P. K. Grover and W. D. Odell, J. Steroid Biochem., 8, 121/1976). The coupling products can then be used for the production of antibodies against the hapten component or as tracers in immunoassays (cf. K. Luebke and B. Nieuweboer, "Immunologische Teste fur niedermolekulare Wirkstoffe", pub. Thieme Verlag, Stuttgart, 1978).

When conjugates of hapten bound to an immunogenic protein via a linking group are used in immunization protocols cross-reactions with the bridge molecule part frequently occur and the antibodies obtained display, in part, a very high affinity for the bridge structures present in the immunogen. In immunological tests, this often gives rise to problems because a part of the binding activity of the antibody is directed against the linker, i.e. against the bridge molecule between hapten and carrier protein in the immunogen. In order to avoid this effect, which often leads to disadvantageous effects in the case of the development of immunoassays, especially for haptens present in low concentrations, the heterologous linker method is preferably used to produce hapten-enzyme conjugates (cf., for example, B. K. van Weemen and A. H. W. M. Schuurs, Immunochem., 12, 667/1975; H. Hosada et al., Chem. Pharm. Bull., 34, 2105/1986), i.e. the linking group in the conjugate is made foreign with regard to the immunogen, i.e. is structurally changed.

If, now, for the production of antibodies, an immunogen is used in which a hapten with a keto or aldehyde function is coupled via 0-(carboxymethyl)-hydroxylamine to the lysine residue of a carrier protein, the following possibilities are known as available heterologous linkers (a) the use of glycine hydrazide as bridge (cf. R. Mueller et al., Hoppe-Seylers Z. Physiol. Chem., 357, 1007/1976; the hydrazide function thereby reacts to give the hydrazone and, via the free amino group of the linker, there subsequently follows the coupling of the hapten derivative to a carboxyl function of the enzyme;

(b) the conversion of the carbonyl function into a hydroxyl function and coupling via an ether or ester function to the bridge molecule (cf. K. Luebke and B. Nieuweboer, loc. cit.; and B. K. van Weeman and A. H. W. M. Schuurs, loc. cit.).

However, both methods suffer from disadvantages: method (a) is limited to enzymes which have free carboxyl groups and which, furthermore, must not be on the reactive center of the enzyme. The coupling reaction takes place with the use of carbodiimide in which case it can generally result in undesired cross-linking reactions of the enzyme. In the case of method (b), the hapten is chemically so substantially changed that the binding to the antibody is disadvantageously influenced.

Therefore, it is an object of the present invention to provide hapten-protein conjugates which lead to the binding of antibodies specifically directed against the hapten and, in the case of use in immunoassays, lead to a specific binding of antibodies to the hapten without cross-reaction with the bridge molecule part occurring. This object is achieved by means of the present invention.

Thus, according to the present invention, there are provided hapten derivatives of the general formula:

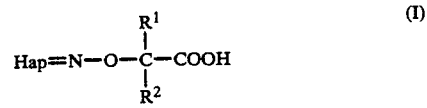

$$\text{Hap}=N-O-\underset{R^2}{\overset{R^1}{C}}-COOH \tag{I}$$

wherein Hap is the residue formed from a hapten carrying keto or aldehyde groups by splitting off an oxo group and $R^1$ and $R^2$, which can be the same or different, are alkyl radicals containing up to 7 and preferably up to 3 carbon atoms and one of the symbols $R^1$ and $R^2$ can also represent a hydrogen atom.

An alkyl radical $R^1$ and $R^2$ containing up to 7 and preferably up to 3 carbon atoms can be straight-chained or branched. The alkyl radical is preferably straight-chained and can be, for example, a methyl, ethyl, n-propyl, n-butyl, n-pentyl, n-hexyl or n-heptyl radical.

The hapten residue in general formula (I) is preferably derived from a steroid hormone, for example testosterone, progesterone, estradiol (via 6-ketoestradiol) or estriol (via 6-ketoestriol).

The hapten derivatives of general formula (I) according to the present invention can be prepared from a hapten carrying a keto or aldehyde group by converting a keto or aldehyde group into the corresponding oxime derivative with a compound of the general formula:

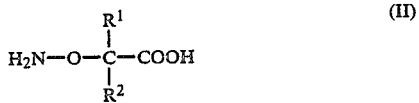

wherein $R^1$ and $R^2$ have the meanings given in general formula (I).

The compounds of general formula (II) are known or can be prepared analogously to a process for the preparation of known compounds (cf. K. S. Suresh and R. K. Malkani, Ind. J. Chem., 10, 1068/1972).

The conversion of the keto or aldehyde groups into the oxime by reaction of the hapten with a compound of general formula (II) can take place in the manner generally known for such oxime formation. Condensation to give the oxime takes place, for example, by reaction with an appropriate hydrochloride or hydrobromide of a carboxyalkylamine of general formula (II) under alkaline conditions.

If the hapten does not possess an appropriate functional group (oxo group), then this can be introduced for the condensation, for example into the 6-position of a steroid hormone. In any case, the condensation of the hapten with the compound of general formula (II) must take place in such a way that its epitope remains freely accessible after the condensation. After the reaction with the hapten, protective groups which have possibly been introduced into the hapten are split off in known manner.

The present invention also provides hapten-protein conjugates of the general formula:

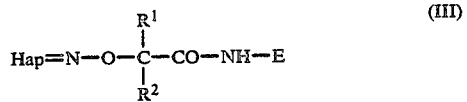

wherein Hap, $R^1$ and $R^2$ have the meanings given in general formula (I) and E—NH— is the residue of a protein bound via an $\epsilon$-amino group of a lysine residue.

In a preferred embodiment of the hapten-protein conjugate of general formula (III) according to the present invention, the hapten is a steroid hormone and especially preferably testosterone but can also be an enzyme, especially preferably $\beta$-galactosidase or peroxidase.

The hapten-protein conjugates of general formula (III) can be prepared by reacting a hapten derivative of general formula (I) according to the present invention with a protein E—NH$_2$ in which —NH$_2$ is an $\epsilon$-amino group of a lysine residue.

The reaction of the hapten derivative of general formula (I) with the $\epsilon$-amino group can be carried out selectively in known manner by conversion of the carboxyl group of the hapten derivative of general formula (I) into an activated ester and especially into the corresponding N-hydroxysuccinimide ester (cf. K. Luebke and B. Nieuweboer, loc. cit.).

In the hapten-protein conjugate of general formula (III), the hapten residue Hap is preferably one of the residues mentioned as being preferable for the hapten derivatives of general formula (I).

The preferred meaning of the protein residue E depends especially upon the intended use of the hapten-protein conjugate according to the present invention. For the immunization of organisms which are form antibodies, the protein is an immunogenic protein and especially one of the immunogenic proteins usually employed, for example edestin or bovine serum albumin. For use in immunoassays, there are preferably employed the enzymes usually employed in immunoassays, $\beta$-galactosidase or peroxidase are preferred.

In one embodiment of the present invention, hapten-protein conjugates are provided in which the hapten is a steroid hormone. The detection of steroid hormones, for example estrogen, testosterone, cortisone and the heart glucosides, the steroid structure of which is common to all of them, is very important for diagnosis. The making available of antibodies against steroid hormones, as well as of steroid hormone-enzyme conjugates for the carrying out of immunoassays, is, therefore, desirable. It has now proved to be very advantageous possibly so to derivatize steroid hormones that they carry an oxo group on the C6 atom. This oxo group can then be reacted with carboxyalkoxyamines of general formula (II) to give hapten derivatives of general formula (I). This binding does not impair the epitope of the steroid hormone and does not lead to any undesired changes in the molecule. Depending upon the purpose of use, the hapten derivative can be coupled either to an immunogenic protein or to an enzyme.

In the case of use for immunization, a conjugate is preferably used in which the protein is an immunogenic carrier protein, for example edestin or bovine serum albumin. However, conjugates which contain an enzyme as protein can also be used for the immunization. The conjugate according to the present invention is injected several times at intervals into the host organism. The conjugate then brings about the formation of antibodies which, in a very high percentage, are only directed against the hapten and display no cross-reactivity with the linking group. The antibodies can then be obtained from the organism in known manner. The hapten-carrier conjugates used according to the present invention are appropriate not only for immunization for the production of polyclonal antibodies but also for the production of monoclonal antibodies.

In a further embodiment of the present invention, a hapten-protein conjugate of the general formula (III) according to the present invention of a hapten which is bound to an enzyme via the linking grouping according to the present invention is used for carrying out immunoassays. The hapten-enzyme conjugate according to the present invention can then be used as label (labelling enzyme) in determination processes according to the immunoassay principle. The hapten-enzyme conjugate according to the present invention can be added, for example, in known amount to a sample solution and then competes for an antibody directed against the hapten.

Surprisingly, by means of the use of a hapten-protein conjugate according to the present invention, it is possible to obtain antibodies which show very little cross-reactivity with the bridge compound, and which have a high affinity to the hapten. When hapten-protein conjugates according to the present invention for immunization are used, high antibody titers are obtained. Furthermore, the hapten-protein conjugates according to the present invention are especially well suited for use in immunoassays. Since the antibodies show no or very little affinity to the bridge molecule and, therefore, bind the hapten very specifically, when these conjugates are used in immunoassays, very exact results are obtained.

The hapten derivatives of general formula (I) according to the present invention have the advantage that, on the one hand, they maintain the structure of the free hapten substantially unchanged and, on the other hand, in comparison with derivatives which have been produced analogously with 0-(carboxymethyl)-hydroxylamine, display a characteristic change in the bridge molecule. Therefore, the use of the hapten derivatives according to the present invention makes possible the carrying out of heterologous linker techniques in a simple and effective way. For the two purposes of use as
1. immunogen and
2. conjugate in immunological analysis there are preferably used different bridges in the hapten-protein conjugate according to the present invention (at least one of the radicals $R^1$ or $R^2$ is different, in which case, for one of the two purposes of use, there can also be used derivatives which are derived from 0-(carboxymethyl)-hydroxylamine, i.e. $R^1$ and $R^2$ are hydrogen atoms) which, however, on the other hand, should again be as similar as possible in order to maintain the specificity.

Therefore, the present invention is also concerned with the use of a hapten-protein conjugate according to the present invention of general formula (III) for the immunisation of organisms suitable for the formation of antibodies and as labelling enzyme in an immunoassay.

The following Examples are given for the purpose of illustrating the present invention, reference being made to the accompanying drawing in which FIG. 1 shows the results of a testosterone determination with the testosterone-3-dmc-POD conjugate according to the present invention in comparison with testosterone-3-cmo-POD.

EXAMPLE 1

Preparation of testosterone-3-dimethylcarboxymethoxime-POD conjugate (testosterone-3-dmc-POD; formula (III): $R^1=R^2=$methyl, Hap=testosterone residue, E—NH=peroxidase residue)

The preparation takes place according to the following reaction scheme:

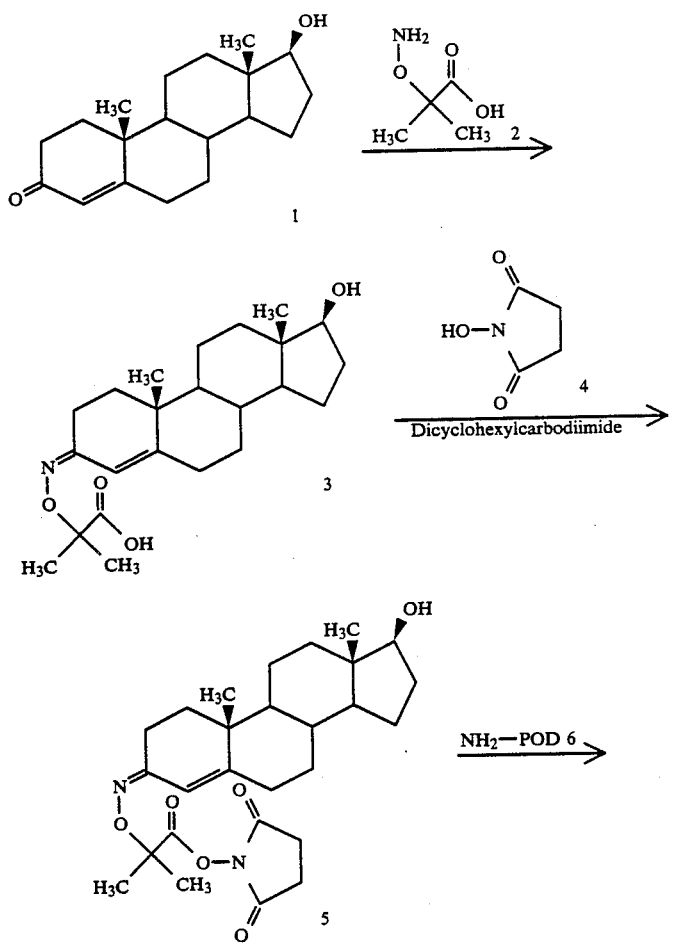

-continued

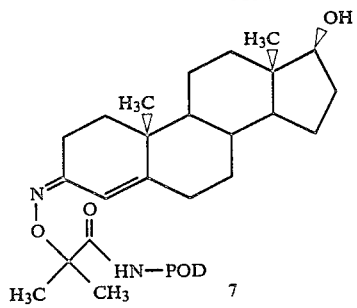

1. Testosterone-3-dimethylcarboxymethoxime (3)

2.88 g. (10 mMole) testosterone (1) were dissolved in 50 ml. methanol, mixed with 1.65 ml. (20 mMole) pyrrolidine and stirred at 20° C. After a short time, a precipitate formed in the yellow solution. After 10 minutes, 2.1 g. (10.5 mMole) 2-aminooxyisobutyric acid hydrobromide (2) (prepared according to the procedure of K. D. Suresh and R. K. Malkani, Ind. J. Chem., 10, 1068/1972) were added thereto and the reaction mixture heated for 5 minutes to 65° C. Thereafter, the solution was evaporated under waterpump vacuum, the residue was mixed with 50 ml. 1 mole/liter sodium hydroxide solution and subsequently dissolved in 2 liters of water. The almost clear solution was washed twice with, in each case, 250 ml. ethyl acetate. The alkaline phase was adjusted with concentrated hydrochloric acid to pH 1 and extracted twice with, in each case, 200 ml. ethyl acetate. The ethyl acetate extract was then washed with 0.5 liters of water, dried with 20 g. anhydrous sodium sulphate and evaporated in a vacuum. The residue was digested with petroleum ether, the suspension was stirred for about 2 hours and the solid product (3) was filtered off with suction. It was dried in a desiccator over phosphorus pentoxide.

Yield: 1.8 g. (46% of theory).

TLC: silica gel; chloroform/methanol/glacial acetic acid (66/33/1 v/v/v); $R_f = 0.69$.

2. Testosterone-3-dimethylcarboxymethoxime N-hydroxysuccinimide ester (5)

0.97 g. (2.5 mMole) of the carboxylic acid (3) was dissolved with 0.35 g. (3 mMole) N-hydroxysuccinimide (4) in 20 ml. tetrahydrofuran and mixed with 0.62 g. (3 mMole) dicyclohexylcarbodiimide in 10 ml. tetrahydrofuran. The reaction mixture was stirred for 3 hours at 20° C., then filtered off from the precipitated dicyclohexylurea and the filtrate evaporated under waterpump vacuum. The residue was dissolved in 50 ml. dioxan and the solution cooled for 16 hours at 4° C. It was then filtered and the solvent removed from the filtrate in a vacuum. The oily residue was digested with 50 ml. diisopropyl ether until it had solidified completely. The product (5) was filtered off with suction and dried over phosphorus pentoxide in a desiccator. Yield: 0.86 g. (70% of theory).

TLC: silica gel; chloroform/methanol/glacial acetic acid (80/19/1 v/v/v); $R_f = 0.70$.

3. Testosterone-3-dimethylcarboxymethoxime-POD conjugate (7)

35 mg. Peroxidase (POD) (EC 1.11.1.7) were dissolved in 3.5 ml. 0.1M potassium phosphate solution (pH 8.0), cooled to 4° C. and slowly mixed with 3.3 ml. dimethyl sulphoxide.

5 mg. of the testosterone-3-dimethylcarboxymethoxime N-hydroxysuccinimide ester (5) described above under 2 were dissolved at ambient temperature in 200 $\mu$l. dimethyl sulphoxide and added in 6 equal portions to the cold peroxidase solution at intervals of about 30 minutes. The reaction mixture was stirred overnight at 4° C.

For the separation of the free ester, a column (2 cm. diameter, 16 cm. height) was packed with Sephadex G 25 fine (Pharmacia) and equilibrated at 4° C. with 40 mMole/liter potassium phosphate solution (pH 6.5). The total conjugate solution was applied to the column at 4° C. at a rate of one column volume/hour and eluted with the same rate of flow with equilibration buffer. The eluate was collected in fractions and the red-brown coloured fractions were collected. The combined conjugate fractions were saturated with thymol and stored at 4° C.

EXAMPLE 2

Testosterone determination with testosterone-3-carboxymethoxime (cmo)-POD.

Reagents

Test buffer

400 $\mu$g./ml. monoclonal antibodies against testosterone (ECACC 85121701)

40 mMole/liter sodium phosphate (pH 6.8).

Loading solution

10 $\mu$g./ml. polyclonal sheep antibody (IgG) against mouse Fc-gamma 20 mMole/liter sodium carbonate buffer (pH 9.6)

Wash solution 250 mg./100 ml. sodium chloride 1 mg./100 ml. copper sulphate

Substrate solution 1.9 mMole/liter ABTS® (2,2''-azino-di-[3-ethylbenzthiazoline-6-sulphonic acid diammonium salt] 100 mMole/liter phosphate-citrate buffer (pH 4.4) 3.2 mMole/liter sodium perborate

Sample

As sample, there was used testosterone in different concentrations in buffer solution:

40 mMole/liter sodium phosphate (pH 7.4)

0.9% sodium chloride 0.3% bovine serum albumin 0.2% Pluronic PF 68.

For carrying out the determination, 1 ml. of coating solution was incubated at ambient temperature for 30 minutes in a Luran test tube. Subsequently, the test tube was washed twice with wash solution. 1 ml. of test buffer was added thereto, incubated for 60 minutes at ambient temperature and washed twice with wash solution. 50 μl. of sample and 1 ml. testosterone-3-cmo-POD (200 mU/ml.) in 40 mMole/liter sodium phosphate buffer (pH 6.8) with 0.2% Pluronic PF 68 were added thereto, incubated for 30 minutes at ambient temperature and washed twice with wash solution. Thereafter, 1 ml. of substrate solution was added thereto, incubated for 30 minutes at ambient temperature and the extinction measured at 405 nm.

EXAMPLE 3

Testosterone determination with testosterone-3-dmc-POD conjugate

The determination was carried out as described in Example 2 except that testosterone-3-dmc-POD conjugate was used instead of testosterone-3-cmo-POD conjugate.

The results of Examples 2 and 3 can be seen from FIG. 1. It can be seen therefrom that, with the conjugate according to the present invention, there is obtained a calibration curve (curve 2) which is substantially steeper in the lower concentration range than with a cmo conjugate (curve 1) so that, for a testosterone test using the conjugate according to the present invention, a substantially greater sensitivity is obtained.

EXAMPLE 4

Preparation of oestradiol-6-dimethylcarboxymethoxime-POD conjugate

The preparation takes place according to the following reaction scheme:

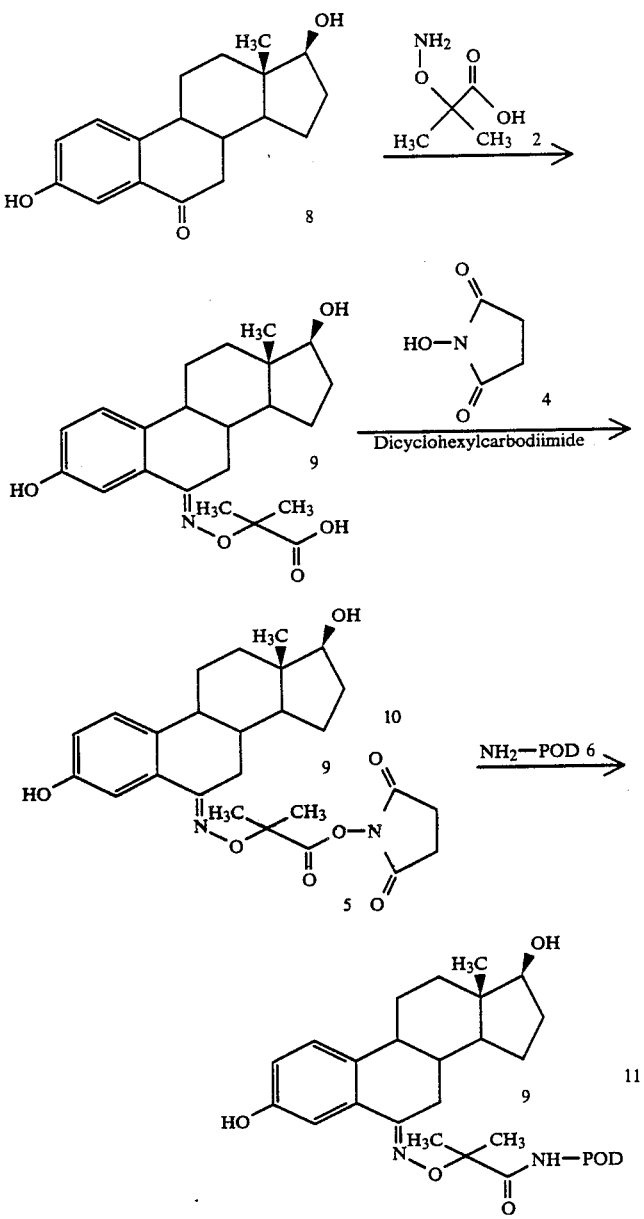

(a) Estradiol-6-dimethylcarboxymethoxime (9)

2.86 g. (10 mMole) 6-oxoestriol (8) were dissolved in 130 ml. ethanol and mixed with 1.7 g. (20 mMole) sodium hydrogen carbonate and 2.1 g. (10.5 mMole) 2-aminooxyisobutyric acid hydrobromide (2). The reaction mixture was heated for 30 minutes to 65° C., whereafter the solution was evaporated under waterpump vacuum, the residue was mixed with 50 ml. 1N sodium hydroxide solution and subsequently dissolved in 1 liter of water. The almost clear solution was washed twice with, in each case, 150 ml. ethyl acetate. The alkaline phase was isolated, adjusted with concentrated hydrochloric acid to pH 1 and extracted twice with, in each case, 150 ml. ethyl acetate. The ethyl acetate extract was washed with 0.25 liters of water, dried with 10 g. anhydrous sodium sulphate and evaporated in a vacuum. The residue was digested with petroleum ether, the suspension was stirred for about 2 hours and the solid product (9) was filtered off with suction. It was dried in a desiccator over phosphorus pentoxide. Yield: 3.10 g. (80% of theory).

TLC: silica gel, ethyl acetate: $R_f=0.58$.

(b) Estradioldimethylcarboxymethoxime N-hydroxysuccinimide ester (10).

970 mg. (2.5 mMole) of the carboxylic acid (9) were dissolved with 350 mg. (3 mMole) N-hydroxysuccinimide (4) in 30 ml. dry tetrahydrofuran and mixed with 620 mg. (3 mMole) dicyclohexylcarbodiimide in 10 ml. tetrahydrofuran. The reaction mixture was stirred for 3 hours at 20° C., then filtered off from the precipitated dicyclohexylurea and the solution evaporated under waterpump vacuum. The residue was dissolved in 25 ml. tetrahydrofuran and the solution cooled to 4° C. for 16 hours. It was then filtered and the solvent removed in a vacuum. The oily residue was digested with 20 ml. isopropanol until it had completely solidified. The product (10) was filtered off with suction, washed with 50 ml. diisopropyl ether and dried in a desiccator over phosphorus pentoxide. Yield: 940 mg. (78% of theory).

TLC: silica gel RP-18, nitromethane/ethanol (9:1 v/v); $R_f=0.70$.

(c) Estradiol-6-dimethylcarboxymethoxime-POD conjugate.

This was prepared analogously to (7) (see Example 1, 3).

I claim:

1. Steroid-hapten-protein conjugate of the formula:

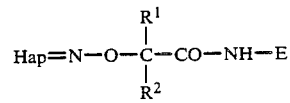

wherein Hap is a steroid hapten residue, $R^1$ and $R^2$, which can be the same or different are hydrogen or alkyl radicals containing from 1 to 7 carbon atoms and E—N—H is a protein residue bound via an ε-amino group of a lysine residue with the proviso that when one of $R^1$ and $R^2$ is hydrogen the other is not.

2. Steroid-hapten-protein conjugate of claim 1, wherein the hapten is a steroid hormone.

3. Steroid-hapten-protein conjugate of claim 2, wherein the steroid hormone is testosterone.

4. Steroid-hapten-protein conjugate of claim 1 wherein the protein is an enzyme.

5. Steroid-hapten-protein conjugate of claim 4, wherein the enzyme is β-galactosidase or peroxidase.

6. Steroid-hapten-protein conjugate of claim 1, designated testosterone-3-dimethylcarboxymethoxime-peroxidase.

7. Steroid-hapten-protein conjugate of claim 1, designated estradiol-6-dimethylcarboxymethoxime peroxidase.

8. Method for producing an antibody specific for a steroid-hapten and not cross reactive with a bridge molecule to which said steroid-hapten or a derivative thereof is bound, comprising immunizing a host animal with a derivative of claim 1 so as to provoke an immune response.

9. Method for determining a steroid in a sample comprising adding a steroid-hapten-protein conjugate of claim 4 and an antibody which binds to both steroid and steroid-hapten protein conjugate to a sample and measuring binding or lack thereof of said conjugate to said antibody as a determination of said steroid in said sample.

* * * * *